United States Patent [19]

Fujii

[11] Patent Number: 4,862,894

[45] Date of Patent: Sep. 5, 1989

[54] APPARATUS FOR MONITORING BLOODSTREAM

[76] Inventor: Hitoshi Fujii, 818, North 25 West 13, Kita-Ku, Sapporo-shi, Hokkaido, Japan

[21] Appl. No.: 160,800

[22] Filed: Feb. 26, 1988

[30] Foreign Application Priority Data

Mar. 3, 1987 [JP] Japan ................................. 62-48058
Nov. 7, 1987 [JP] Japan ................................. 62-281490

[51] Int. Cl.⁴ .............................................. A61B 5/02
[52] U.S. Cl. ..................................... 128/666; 128/691
[58] Field of Search .............................. 128/664–667, 128/632–634, 637, 691; 356/39–42

[56] References Cited

U.S. PATENT DOCUMENTS

| | | | |
|---|---|---|---|
| 3,511,227 | 5/1970 | Johnson | 128/666 |
| 3,591,290 | 7/1971 | Zinner | 128/633 X |
| 4,109,647 | 8/1978 | Stern et al. | 128/666 |
| 4,366,381 | 12/1982 | Fischer et al. | 128/664 X |
| 4,412,543 | 11/1983 | Vassiliadis et al. | 128/665 X |
| 4,446,871 | 5/1984 | Imura | 128/633 |
| 4,586,190 | 4/1986 | Tsuji | 356/39 X |
| 4,590,948 | 5/1986 | Nilsson | 128/666 |
| 4,596,254 | 6/1986 | Adrian et al. | 128/666 |
| 4,703,758 | 11/1987 | Omura | 128/672 |

FOREIGN PATENT DOCUMENTS 8800447 1/1988 PCT Int'l Appl. ................. 128/637

Primary Examiner—Kyle L. Howell
Assistant Examiner—Angela D. Sykes
Attorney, Agent, or Firm—Peter J. Georges

[57] ABSTRACT

An apparatus for monitoring a bloodstream in a skin surface including a laser light source for emitting a laser beam, a cylindrical lens for expanding the laser beam, an objective lens for collecting light rays reflected by the skin surface and scattered by blood cells, a linear image sensor for receiving the reflected light rays via an objective lens, A/D converter for converting output signals read out of light receiving elements of the linear image sensor into digital signals, a memory for storing the digital signals, a calculating circuit for calculating a bloodstream velocity or a distribution of bloodstream, and a display device for displaying the bloodstream velocity or the distribution of bloodstream.

11 Claims, 3 Drawing Sheets

APPARATUS FOR MONITORING BLOODSTREAM

BACKGROUND OF THE INVENTION

Field of the Invention and Related Art Statement

The present invention relates to an apparatus for monitoring a bloodstream flowing through a blood vessel, and more particularly to an apparatus for measuring a distribution and a variation in time of an average velocity of bloodstream in a skin surface of a patient by means of the laser speckle method.

When laser light is made incident upon a living tissue such as a skin, the laser light is scattered by particles constituting the blood, and scattered light rays are interfered with each other to form random pattern, i.e. speckle pattern. This speckle pattern changes in time due to the movement of the blood cells in the blood vessel. Therefore there can be derived a noise-like signal representing the velocity of the bloodstream by measuring the variation in time of the intensity of light scattered at a certain point on the skin. This phenomenon was found by Dr. M. D. Stern et al around the year of 1975. By utilizing this phenomenon, the bloodstream can be measured with the aid of the frequency analysis of the speckle signal without damaging the skin. The study of this phenomenon has been rapidly developed and the apparatus for monitoring the bloodstream has been commercially available as the laser Doppler bloodstream meter.

In the known apparatus, the variation in time of the bloodstream at a point is detected with the aid of an optical fiber scope, or an abnormal condition is detected by comparing the detected data with that at a standard point. However, in the known laser Doppler bloodstream meter using the optical fiber, since an area of the detection point has a very small diameter such as several millimeters, the measured data fluctuates for respective measuring points. Therefore, it is not suitable to estimate the bloodstream in a rather large area. Further, since the signal obtained via the optical fiber scope is inherently noisy, there must be provided an integrating circuit or low pass filter for smoothing the noisy signal. When the time constant of these circuits is made large, the variation of the bloodstream can be displayed slowly, but the response to the rapid change in the bloodstream is decreased.

SUMMARY OF THE INVENTION

The present invention has for its object to provide a novel and useful apparatus for monitoring the bloodstream with the aid of the laser speckle method, which can display the variation in time of the bloodstream with a high response as well as the distribution of the bloodstream activity.

According to the invention, an apparatus for monitoring a bloodstream comprises light projecting means for projecting a laser light upon an object; light receiving means including a number of light receiving elements for receiving laser light reflected by the object; memory means for storing output signals read out of the light receiving elements; calculating means for calculating from the output signals stored in said memory means to derive information about a bloodstream of the object; and display means for displaying the information about the bloodstream.

DESCRIPTION OF THE PREFERRED EMBODIMENTS

Figure 1:
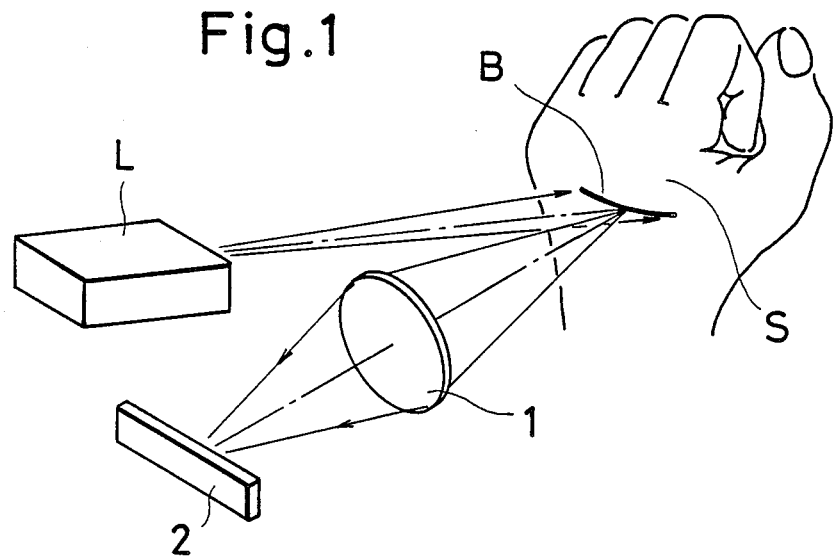
FIG. 1 is a perspective view showing the manner of monitoring the bloodstream in the skin surface with the aid of the apparatus according to the invention.

FIG. 1 is a perspective view showing schematically an embodiment of the bloodstream monitoring apparatus according to the invention. The apparatus comprises a laser light source L for projecting a laser light beam B upon a skin surface S. The laser light source L comprises a laser for emitting a laser beam and a cylindrical lens for converting the laser beam emitted from the laser into a rectilinear beam having a width of several centimeters. The laser light reflected by the skin surface S is made incident upon a linear line sensor 2 via an objective lens 1. The linear line sensor 2 comprises a number of light receiving elements arranged in one direction. On the light receiving surface of the line sensor 2 there is formed the speckle pattern which varies in time in accordance with the movement of blood cells in blood vessels within the skin surface S. Therefore, by scanning the line sensor 2, there may be obtained photoelectric signals representing the variation in time of the speckle pattern.

Figure 2A:
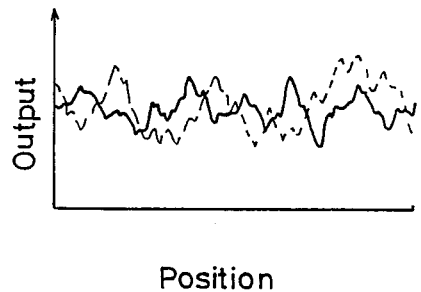
FIGS. 2(a) and 2(b) are graphs illustrating the output signal of the bloodstream monitoring apparatus.
Figure 2B:
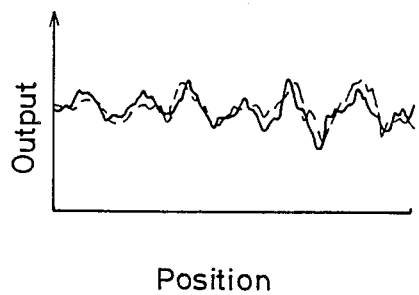

FIGS. 2(a) and 2(b) are graphs showing the variation in time of the output signal from the line sensor 2, while the laser light is made incident upon the skin surface S at the same point thereof. Solid line and broken curves represent the output signals at different timings. FIG. 2(a) shows the output signal when the bloodstream velocity is high, and the curve shown in FIG. 2(b) denotes the condition in which the velocity of the bloodstream is low. In FIG. 2(a), the output signal at the second timing is greatly different from that of the first timing due to the large variation of the speckle pattern. On the contrary, the output signals at the first and second timings shown in FIG. 2(b) are substantially same with each other, because the variation of the speckle pattern is small. Therefore, when differences between the output signals from successive image sensing elements at different timings are derived and are accumulated, an accumulated value becomes large for FIG. 2(a) and small for FIG. 2(b). By effecting the operation at a high speed, it is possible to trace the variation in time of an average velocity of the bloodstream along a given line.

Figure 3:
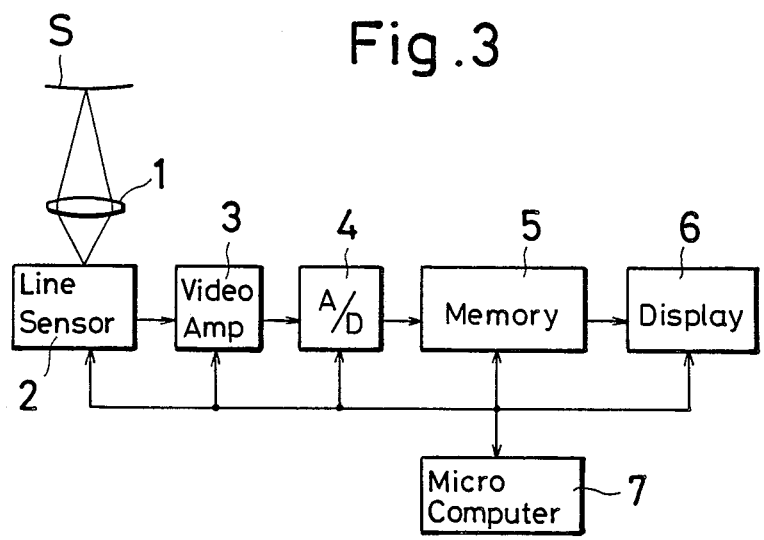
FIG. 3 is a block diagram depicting the construction of the signal processing unit of the bloodstream monitoring apparatus.

FIG. 3 is a block diagram showing a signal processing unit. An output signal from the line sensor 2 is successively supplied to video amplifier 3, A/D converter 4, memory 5 and display 6. These circuits are connected to a micro computer 7 and are controlled by the micro computer and signals are transmitted between the circuits and the micro computer.

The line sensor 2 comprises 256 light receiving elements and output signals successively read out of the elements are amplified by the video amplifier 3 and are converted into digital signals by the high speed A/D converter 4. These digital signals are then stored in the memory 5. Under the control of the program stored in the micro computer 7, differences between output signals from respective light receiving elements are calculated and then these differences thus calculated are accumulated. The calculation is carried out in the following manner.

Now it is assumed that the number of light receiving elements of the line sensor 2 is N, and output signals from $n^{th}$ light receiving element at timings t and $t+\Delta t$ are expressed by $I(t,n)$ and $I(t+\Delta t,n)$, respectively. Then, the accumulation value $V(t)$ can be calculated as follows.

$$V(t) = \sum_{n=1}^{N} |I(t,n) - I(t + \Delta t,n)|$$

The accumulated value $V(t)$ is proportional to the average velocity of the bloodstream at the timing t. The above calculation is performed at a high speed, and the calculated value is displayed on the display 6 as a series of waveforms or is supplied to a recorder. In this manner, the variation in time of the bloodstream can be measured.

In the embodiment so far explained, the variation of the bloodstream velocity in time is measured. According to the invention, it is also possible to display the distribution of the bloodstream by changing the program stored in the micro computer 7.

Figure 4A:
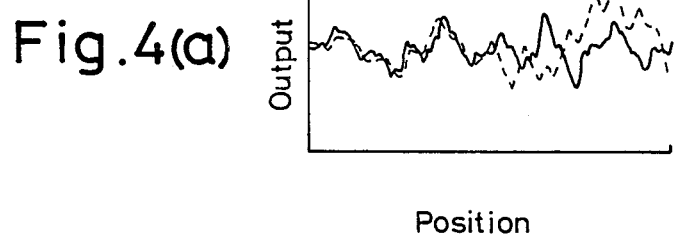
FIGS. 4(a) and 4(b) are graphs illustrating the output signal of the apparatus.
Figure 4B:
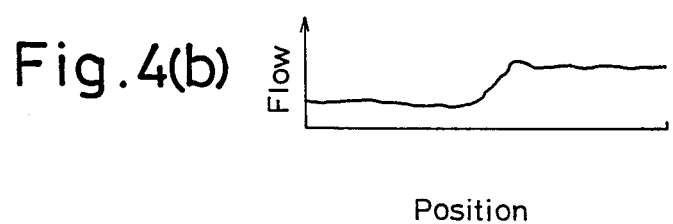

FIG. 4(a) shows output signals read out of the line sensor 2 at successive two timings, while the laser beam is made incident upon a position of the skin surface. In the right hand half of the graph, the blood stream velocity is high, while in the left hand half, the bloodstream velocity is low. In the right hand half, since the pattern shows the large variation, values of the output signals at respective light receiving elements differ largely from each other, but in the left hand half, the differences are small. Therefore, when these differences are accumulated for respective light receiving elements for a predetermined period, it is possible to obtain the distribution of the bloodstream velocity in the scanning line as shown in FIG. 4(b).

The above mentioned calculation is repeated several hundreds times and data thus obtained is stored in the memory 5. Then, under the control of the program stored in the micro computer 7, there are derived differences between the outputs of two successive scannings. This operation may be performed in the following manner.

Now it is assumed that an output signal from $n^{th}$ light receiving element of the line sensor 2 in $k^{th}$ scanning is denoted by $Ik(n)$ and that in $(k+1)^{th}$ scanning is represented by $Ik+1(n)$. Then, an absolute value of a difference between these output signals can be derived as follows.

$$\Delta k(n) = |Ik(n) - k+1(n)|.$$

The differences are accumulated for a number of scanning times M.

$$V(n) = \sum_{k=1}^{M} \Delta k(n)$$

Then, $V(n)$ thus calculated is proportional to the bloodstream velocity at a relevant point. The values $V(n)$ are calculated for respective light receiving elements $(1-N)$ to obtain the distribution of the bloodstream velocity along the measuring line B on the skin surface S. Then the distribution curve is displayed on the display 6 as illustrated in FIG. 4(b)

When at least one of the skin surface S and the measuring system including the objective lens 1 and line sensor 2 is moved in the direction perpendicular to the direction of the scanning line B, it is possible to obtain the two dimensional bloodstream velocity distribution over a certain area of the skin surface S.

Figure 5:
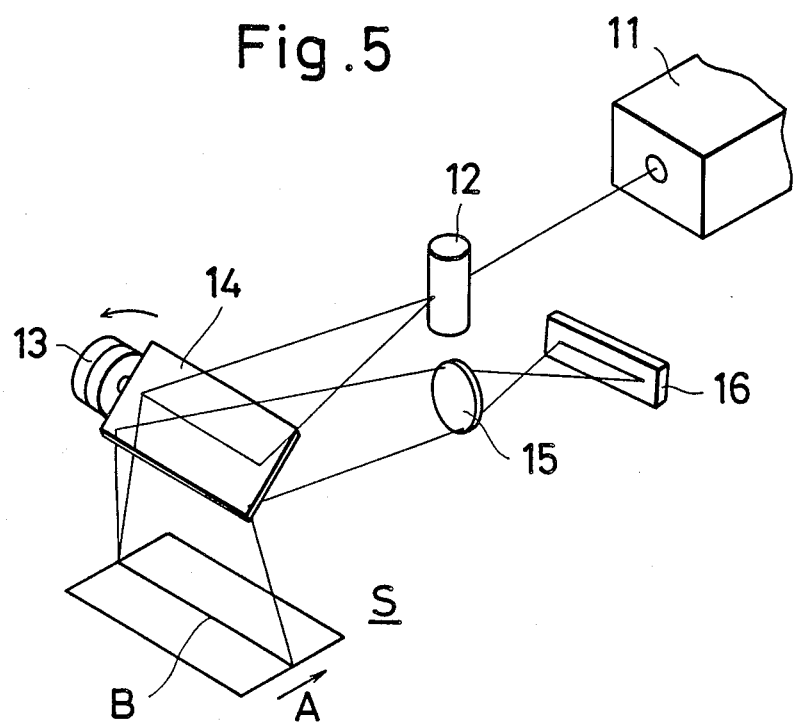
FIG. 5 is a perspective view showing another embodiment of the bloodstream monitoring apparatus according to the invention.

FIG. 5 is a perspective view illustrating another embodiment of the bloodstream monitoring apparatus according to the invention. In the present embodiment, the two dimensional distribution of the bloodstream is measured with the aid of the linear line sensor. A laser light beam emitted from a He-Ne laser light source 11 is expanded in one direction by means of a cylindrical lens 12 and is made incident upon the skin surface S via a reflection mirror 14 which is swung by an electric motor 13 at a constant speed. Therefore, the skin surface S is scanned with the laser beam in a direction A shown in FIG. 5. The laser beam reflected by the skin surface S is reflected again by the swinging mirror 14 and is then made incident upon a line sensor 16 via an objective lens 15.

By swinging the mirror 14 to move the scanning line B in the direction, the skin surface S is scanned two-dimensionally and a two-dimensional map of the bloodstream can be formed. Such a map is quite useful for diagnosis. Further, the color map may be displayed on a color monitor in such a manner that different velocities of the bloodstream velocity are displayed with different colors. With the aid of such a colored map, it is possible to grasp the condition of the bloodstream in fine blood vessels at a glance. Such a colored map may be effectively used together with the thermography.

In the above embodiments, the scattered light is detected by the linear line sensor, but it is also possible to detect the scattered light by means of a two-dimensional image sensor. By using the two-dimensional line sensor, the variation in time of the bloodstream velocity and the bloodstream distribution may be detected two-dimensionally. In this case, the laser beam expanded in two orthogonal directions has to be made incident upon the object.

Moreover, when the sensitivity of the two-dimensional image sensor, i.e. CCD or the output power of the laser light source is sufficiently high, the useful data may be obtained without moving the object and measuring system relative to each other by expanding the laser light two-dimensionally.

As explained above, in the bloodstream monitoring apparatus according to the invention, it is possible to display the variation of the bloodstream and the distribution of the bloodstream which are very useful for the diagnosis. As compared with the known laser Doppler bloodstream meter using the optical fiber probe, the response for the bloodstream change is very high and the field of detection can be made wider.

What is claimed is:

1. An apparatus for monitoring a bloodstream, comprising light projecting means for projecting a laser light upon an object having a bloodstream, comprising a laser light source for emitting a coherent laser beam and an optical system for projecting the coherent laser beam onto a surface of said object at a plurality of points which are arranged at least linearly;

light receiving means, comprising a plurality of light receiving elements arranged at least two-dimensionally to receive a plurality of laser beams scattered by blood cells at said plurality of points on said surface;

memory means for storing output signals read out of the light receiving elements;

calculating means for calculating from the output signals stored in said memory means to derive information about said bloodstream; and display means for displaying said information.

2. An apparatus according to claim 1, wherein said laser light source comprises a He-Ne laser.

3. An apparatus according to claim 1, wherein said light receiving means comprises an objective lens for collecting light rays reflected by the object, and a linear image sensor having said light receiving elements.

4. An apparatus according to claim 3, wherein said laser light projecting means further comprises a mirror arranged rotatably about an axis which extends in said one direction, and an electric motor for rotating the mirror, whereby said objective lens is arranged between the mirror and the linear image sensor.

5. An apparatus according to claim 1, wherein said optical system comprises a cylindrical lens.

6. An apparatus according to claim 1, wherein said laser light projecting means comprises a laser light source for emitting a laser beam, and an optical element for expanding the laser beam in two orthogonal directions, and said light receiving means comprises a two dimensional image sensor.

7. An apparatus according to claim 1, wherein said calculating means calculates an average velocity of the bloodstream.

8. An apparatus according to claim 7, wherein said calculating means performs the following calculation;

$$V(t) = \sum_{n=1}^{N} |I(t,n) - I(t + \Delta t, n)|,$$

wherein N is the number of the light receiving elements, $I(t,n)$ is an output of $n^{th}$ light receiving element at a sampling time t, and $I(t+\Delta t, n)$ is an output of $n^{th}$ light receiving element at a next sampling time $t+\Delta t$.

9. An apparatus according to claim 1, wherein said calculating means calculates a distribution of the bloodstream.

10. An apparatus according to claim 9, wherein said calculating means performs the following calculation;

$$V(n) = \sum_{k=1}^{M} \Delta k(n),$$

wherein $\Delta k(n) = |Ik(n) - Ik+1(n)|$, $Ik(n)$ and $Ik+1(n)$ are outputs of $n^{th}$ light receiving element at $k^{th}$ and $(k+1)^{th}$ samplings, respectively, and M is the number of scannings.

11. An apparatus according to claim 9, wherein said display means comprises a color monitor for displaying different levels of said distribution of the bloodstream with different colors.

* * * * *